(12) United States Patent
Arima

(10) Patent No.: US 11,648,154 B2
(45) Date of Patent: May 16, 2023

(54) METHOD FOR MANUFACTURING WORN ARTICLE

(71) Applicant: ZUIKO CORPORATION, Osaka (JP)

(72) Inventor: Takashi Arima, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 0 days.

(21) Appl. No.: 17/613,167

(22) PCT Filed: May 15, 2020

(86) PCT No.: PCT/JP2020/019396
§ 371 (c)(1),
(2) Date: Nov. 22, 2021

(87) PCT Pub. No.: WO2020/241300
PCT Pub. Date: Dec. 3, 2020

(65) Prior Publication Data
US 2022/0202625 A1    Jun. 30, 2022

(30) Foreign Application Priority Data
May 31, 2019    (JP) .............................. JP2019-102313

(51) Int. Cl.
*A61F 13/15*    (2006.01)
(52) U.S. Cl.
CPC .. *A61F 13/15593* (2013.01); *A61F 13/15699* (2013.01); *A61F 13/15739* (2013.01); *A61F 13/15747* (2013.01)
(58) Field of Classification Search
None
See application file for complete search history.

(56) References Cited

U.S. PATENT DOCUMENTS

| | | | |
|---|---|---|---|
| 8,545,654 B2 * | 10/2013 | Lakso | A61F 13/493 |
| | | | 156/271 |
| 2006/0254708 A1 * | 11/2006 | Wada | A61F 13/15699 |
| | | | 156/271 |

(Continued)

FOREIGN PATENT DOCUMENTS

| | | |
|---|---|---|
| JP | 2005-65971 A | 3/2005 |
| JP | 2014-64627 A | 4/2014 |

(Continued)

OTHER PUBLICATIONS

International Search Report for corresponding Application No. PCT/JP2020/019396, dated Aug. 4, 2020.

*Primary Examiner* — Barbara J Musser
(74) *Attorney, Agent, or Firm* — Renner, Otto, Boisselle & Sklar, LLP

(57) ABSTRACT

A method including: a step of carrying first and second continuous webs in a predetermined carrying direction; a first slitting step of slitting the first continuous web along a virtual first cut-off line extending the carrying direction, thereby dividing the first continuous web into a wider first divided web and a narrower second divided web; a step of sandwiching an around-torso elastic member extending in a girth direction between the wider first divided web and the second continuous web; a welding step of welding together the first divided web, the second continuous web and the around-torso elastic member intermittently in the carrying direction, thereby producing a layered sheet; and a bonding step of sandwiching an around-leg elastic member meandering relative to the carrying direction between the layered sheet and the narrower second divided web, and attaching the around-leg elastic member thereto by an adhesive, thereby producing a stretchable continuous sheet.

24 Claims, 5 Drawing Sheets

(56) References Cited

U.S. PATENT DOCUMENTS

| | | | |
|---|---|---|---|
| 2014/0088542 A1* | 3/2014 | Wilkes | A61F 13/15804 604/385.29 |
| 2017/0014277 A1 | 1/2017 | Matsui | |
| 2018/0140473 A1 | 5/2018 | Koshijima | |
| 2018/0200121 A1 | 7/2018 | Eriksson | |

FOREIGN PATENT DOCUMENTS

| | | | | |
|---|---|---|---|---|
| JP | 2015-198915 A | 11/2015 | | |
| JP | 2018-530376 A | 10/2018 | | |
| WO | WO-2014097928 A1 * | 6/2014 | | A61F 13/15699 |
| WO | 2016/208513 A1 | 12/2016 | | |

* cited by examiner

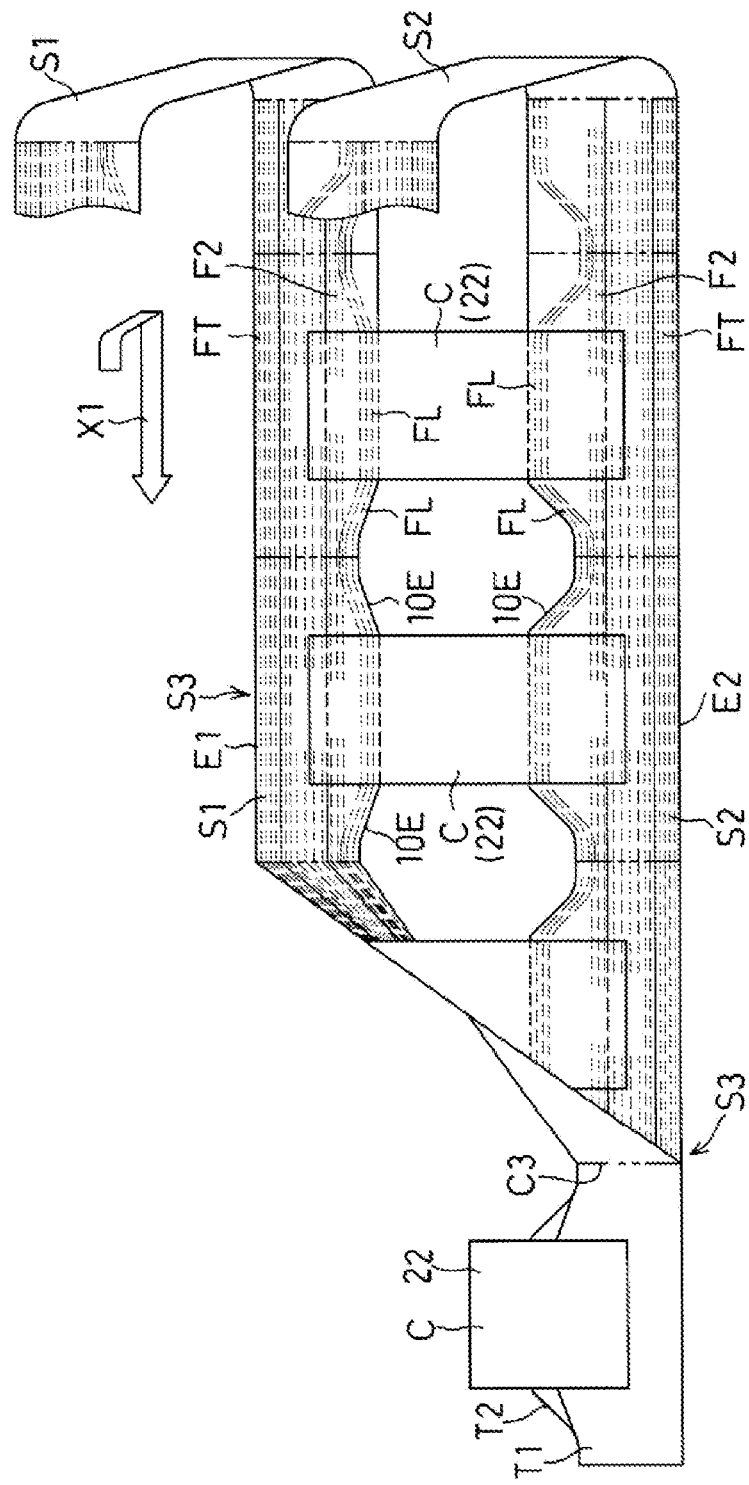

METHOD FOR MANUFACTURING WORN ARTICLE

TECHNICAL FIELD

The present invention relates to a method for manufacturing a worn article, and more particularly to a method for manufacturing a stretchable sheet to be around-torso portions of disposable diapers and pants.

BACKGROUND ART

A stretchable sheet of this type is desirably provided with around-torso elastic members arranged to extend along the periphery of the torso and parallel to each other, and around-leg elastic members arranged to be curved along the bases of the legs. The around-torso elastic members are arranged to extend parallel to the periphery of the torso so as to make the stretchable sheet fit to the torso. On the other hand, the around-leg elastic members are arranged to be curved along the bases of the legs, thereby preventing leakage of urine, for example.

As a method for arranging elastic members to extend parallel to each other, a method has been proposed in the art, in which elastic members being stretched are sandwiched between two continuous webs, and the three parts are welded together intermittently in the carrying direction (longitudinal direction) of the continuous webs. (First Patent Document)

CITATION LIST

Patent Document

[First Patent Document] WO 2016/208513

SUMMARY OF INVENTION

When welding together elastic members and webs with this conventional technique, there is a need to guide the elastic members into grooves formed in the anvil of the welder so that the elastic members are not cut off during the welding process. Therefore, elastic members to be welded on webs can only be arranged in a straight arrangement parallel to the carrying direction, and it is difficult to arrange them in a curved path.

Thus, the step of arranging elastic members in the straight arrangement and the step of arranging elastic members in a curved arrangement are separate steps. Therefore, there is a need for at least three webs for sandwiching elastic members therebetween, thereby increasing the cost of material fabric and increasing apparatuses for feeding and joining the material fabric, increasing the equipment cost.

Thus, it is an object of the present invention to provide a method for manufacturing a worn article having around-torso and around-leg elastic members, with which the cost of material fabric and the equipment cost are inexpensive.

A method for manufacturing a worn article of the present invention includes:

a step of carrying a first continuous web W1 and a second continuous web W2 in a predetermined carrying direction;

a first slitting step of slitting the first continuous web W1 along a virtual first cut-off line C1 extending in the carrying direction, thereby dividing the first continuous web W1 into a wider first divided web W11 and a narrower second divided web W12;

a step of sandwiching an around-torso elastic member FT extending in a girth direction between the wider first divided web W11 and the second continuous web W2;

a welding step of welding together the first divided web W11, the second continuous web W2 and the around-torso elastic member FT intermittently in the carrying direction, thereby producing a layered sheet S; and a bonding step of sandwiching an around-leg elastic member FL meandering relative to the carrying direction between the layered sheet S and the narrower second divided web W12, and attaching the around-leg elastic member FL to the layered sheet S and the second divided web W12 by an adhesive, thereby producing a stretchable continuous sheet S0.

According to the present invention, the first divided web W11 for sandwiching the around-torso elastic members FT and the second divided web W12 for sandwiching the around-leg elastic members FL are obtained by slitting a single first continuous web W1. Therefore, the number of rolls of material fabric for the continuous webs can be reduced by one. This also reduces the cost of material fabric itself, and the cost of equipment for replacing and joining material fabric.

The around-torso elastic member FT is sandwiched between, and welded to, the first divided web W11 and the second continuous web W2. Therefore, the stretchable continuous sheet S0 is unlikely to be stiff.

On the other hand, the around-leg elastic member FL is sandwiched between the second divided web W12 and the layered sheet S and bonded thereto by an adhesive. Therefore, it is possible to arrange the around-leg elastic member FL in a wave-like pattern that is curved along the bases of the legs.

The carrying direction, as used in the present invention, refers to the longitudinal direction in which a web or a sheet is carried along the longitudinal direction, and the carrying direction changes as the web or the sheet is redirected (turned).

BRIEF DESCRIPTION OF THE DRAWINGS

FIG. 5 is a schematic plan view showing, partially in perspective, a late period of the method for manufacturing a worn article.

DESCRIPTION OF EMBODIMENTS

Figure 1:
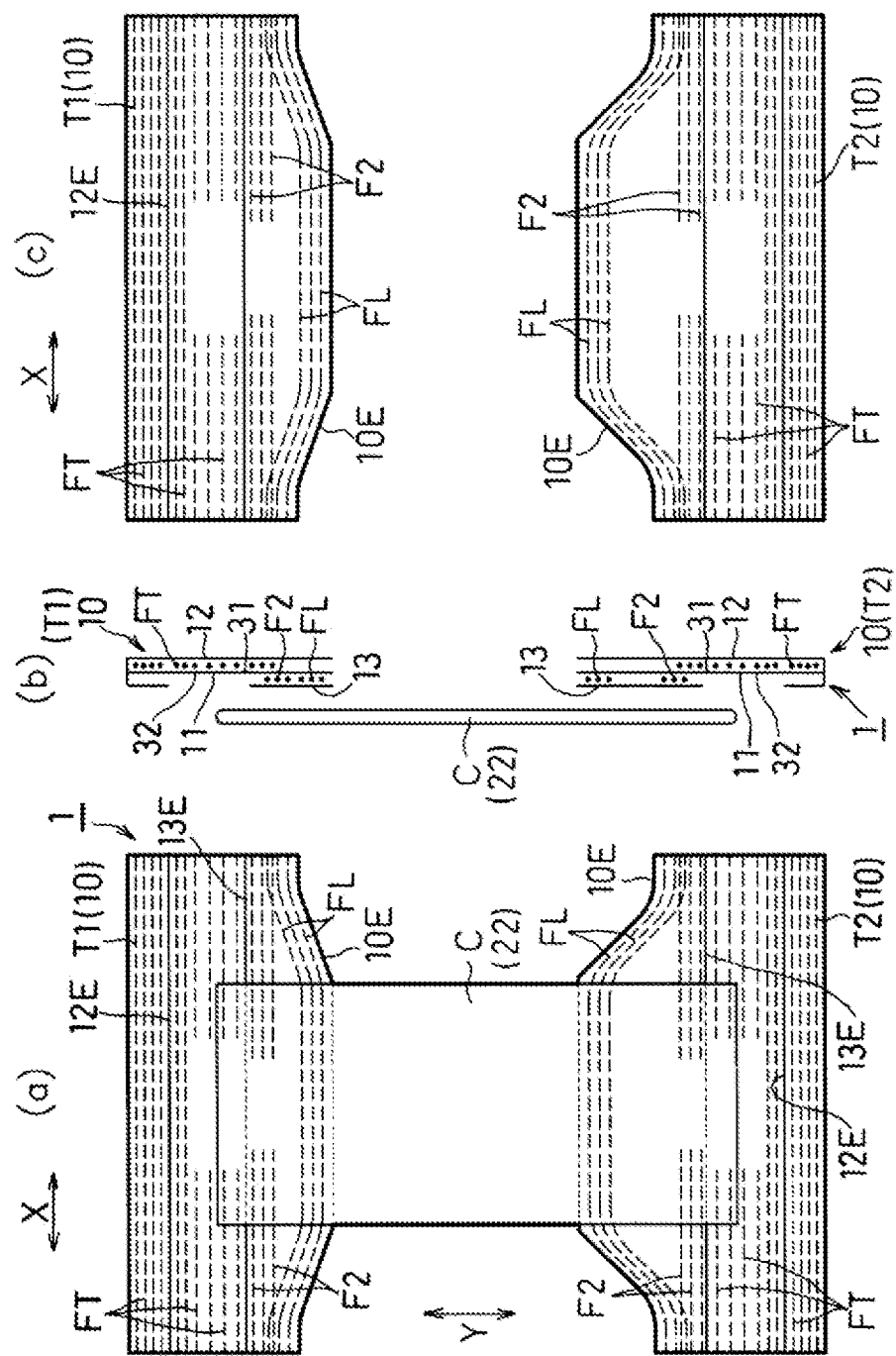
FIG. 1(a) is a schematic plan view showing, flattened, an example of a worn article that is produced by a method for manufacturing a worn article according to one embodiment of the present invention.
FIG. 1(b) is a schematic vertical cross-sectional view showing the worn article.
FIG. 1(c) is a schematic plan view showing a front around-torso portion and a rear around-torso portion with an absorbent body removed.
Figure 2:
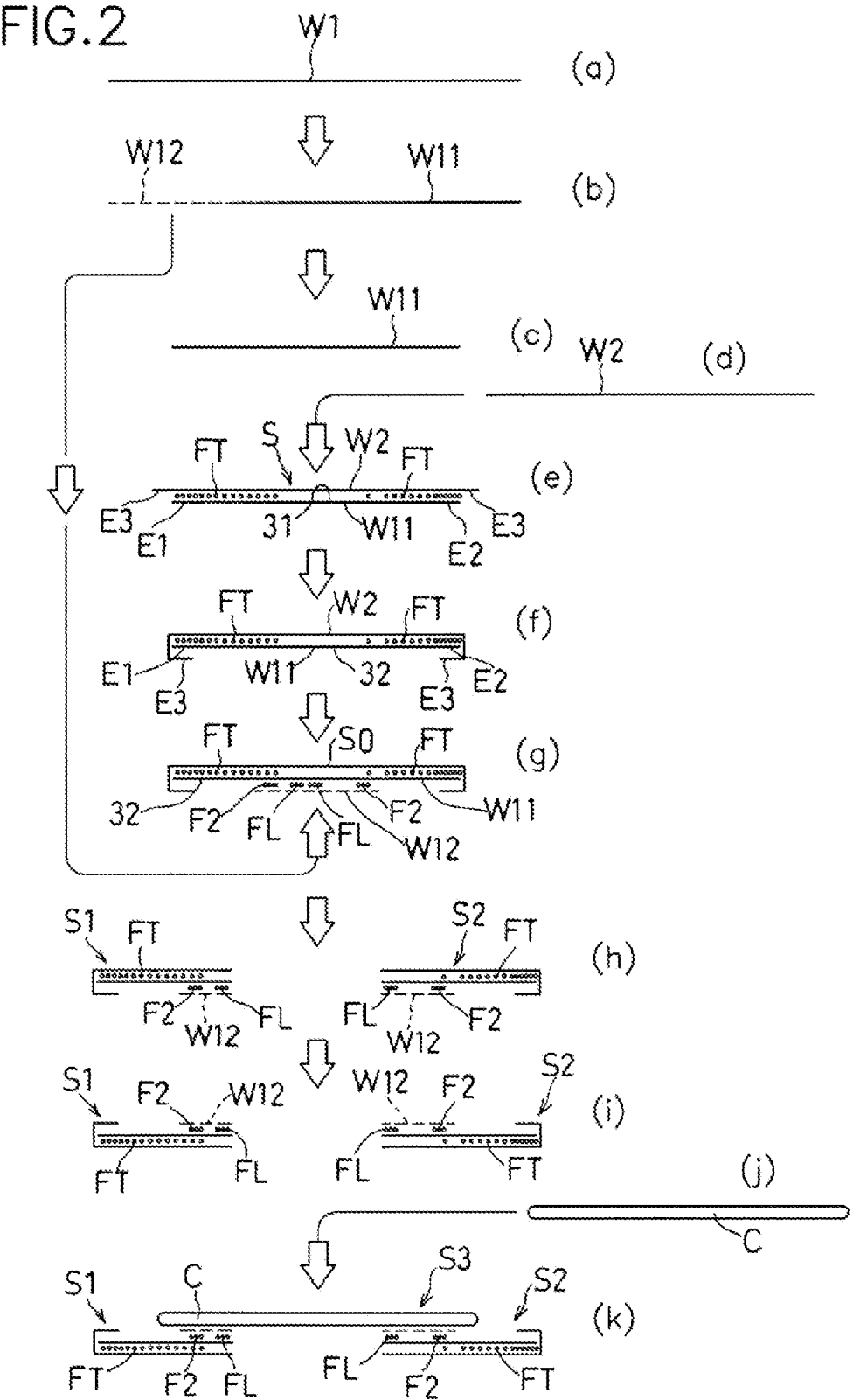
FIGS. 2(a) to 2(k) are cross-sectional views of steps of a method for manufacturing a worn article, showing vertical cross-sectional views of the worn article. Note that in FIG. 2, the second divided web is indicated by a broken line so that the second divided web can be easily recognized.

Preferably in the present invention, a width D11 of the wider first divided web W11 is smaller than a width D2 of the second continuous web W2, and the first divided web W11 has a first side edge E1 and a second side edge E2 along the carrying direction; and the method further comprises a folding back step of folding a pair of third side edges E3 along the carrying direction of the second continuous web W2 so as to wrap the first and second side edges E1, E2 of the layered sheet S.

In order to improve the appearance of the worn article, the side edge of the web is often folded in the upper end area of each around-torso portion. Now, where the side edge of the first divided web W11, which is obtained by dividing the first continuous web W1, is folded, the width of the undivided first continuous web W1 is significantly larger, thereby increasing the bulkiness of the equipment.

In contrast, since the third side edges E3 of the second continuous web W2 are folded in the present example, it is possible to prevent the width of the undivided first continuous web W1 from becoming significantly large.

More preferably, in the welding step, the second continuous web W2 is layered on a first surface 31 of the first divided web W11;

in the folding back step, the third side edges E3 of the second continuous web W2 are folded so as to overlap with a second surface 32 of the first divided web W11; and in the bonding step, the second divided web W12 is bonded to the second surface 32 of the first divided web W11.

In this case, the third side edge E3 of the second continuous web W2 and the edge of the second divided web W12 are both visible on the second surface 32 of the first divided web W11. Therefore, by setting the second surface 32 to be the skin-contact surface side, it is possible to improve the appearance (texture) of the non-skin-contact surface of the worn article.

Preferably in the welding step, the around-torso elastic member FT is arranged along a first side edge E1 and a second side edge E2 along the carrying direction of the layered sheet S;

in the bonding step of producing the stretchable continuous sheet S0, the around-leg elastic member FL is arranged in a central area between the first side edge E1 and the second side edge E2 of the layered sheet S; and the method further comprises a second slitting step of slitting the stretchable continuous sheet S0 along a virtual second cut-off line C2 along the carrying direction, thereby producing a first divided sheet S1 and a second divided sheet S2, the first divided sheet S1 being to be a front around-torso portion T1 including a part of the around-leg elastic member FL, the around-torso elastic member FT arranged on the first side edge E1, and the first side edge E1, and the second divided sheet S2 being to be a rear around-torso portion T2 including a remaining part of the around-leg elastic member FL, the around-torso elastic member FT arranged on the second side edge E2, and the second side edge E2.

In this case, it is possible to produce both of the front around-torso portion T1 and the rear around-torso portion T2 from two, first and second, continuous webs.

Preferably, the method further includes a bridging step of intermittently providing absorbent bodies C so as to bridge between the first divided sheet S1 and the second divided sheet S2, each of the absorbent bodies C connecting together the front around-torso portion T1 and the rear around-torso portion T2 and being to be a crotch portion.

More preferably, the around-leg elastic member FL is arranged in a periodic wave-like pattern in the bonding step of producing the stretchable continuous sheet S0 so that the around-leg elastic member FL arranged on the first divided sheet S1 and the around-leg elastic member FL arranged on the second divided sheet S2 extend close to each other in an area where each of the absorbent bodies C bridges, and the around-leg elastic member FL arranged on the first divided sheet S1 and the around-leg elastic member FL arranged on the second divided sheet S2 extend away from each other in an area between adjacent absorbent bodies C of the absorbent bodies C.

In this case, it is possible to obtain a worn article including the around-leg elastic member FL arranged to extend along the bases of the legs.

Preferably, in the bonding step of producing the stretchable continuous sheet S0, another around-torso elastic member F2 extending straight along the carrying direction is further sandwiched between the layered sheet S and the narrower second divided web W12, and attached thereto by the adhesive, thereby producing the stretchable continuous sheet S0.

In this case, as the other elastic member F2 is arranged in a lower portion of the around-torso area near the around-leg area, it is possible to improve the fitting property of the around-torso portion.

Preferably, the first and second continuous webs W1, W2 are made of a thermoplastic resin; and the welding step is performed by ultrasonic welding or heat sealing.

The thermoplastic first and second webs can easily be welded to elastic members.

Note that each web may be a thermoplastic non-woven fabric obtained by layering together a large number of thermoplastic fibers.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

EMBODIMENTS

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

First, prior to describing the manufacturing method of the present invention, an example of the structure of a worn article 1 will be described with reference to the drawings. Note that the figures show elastic members being stretched.

As shown in FIGS. 1(a) and 1(b), the worn article 1 of the present embodiment has a left-right symmetric shape and a left-right symmetric structure, and includes an absorbent body C and front and rear around-torso portions T1, T2. The front around-torso portion T1 extends in the girth direction X covering the front torso of the wearer. The rear around-torso portion T2 extends in the girth direction X covering the rear torso of the wearer. The absorbent body C is provided so as to bridge between the around-torso portions T1, T2, and includes a crotch portion 22 covering the crotch of the wearer.

The absorbent body C extends in the vertical direction Y being orthogonal to the girth direction X. The absorbent body C accounts for a part or whole of the crotch portion 22.

Although not shown in the figures, the crotch portion 22, in the form of a finished product, is folded in two along a line parallel to the girth direction X. Thus, the worn article may be a pants-type worn article wherein end portions of the front and rear around-torso portions T1, T2 in the girth direction X are attached (sealed) together while overlapping with each other.

An absorbent core (not shown) is provided on the absorbent body C. The absorbent core absorbs body fluid. The absorbent core is sandwiched between a top sheet and a back sheet. The sheets and the absorbent core are layered together.

The top sheet is made of a thin liquid-permeable nonwoven fabric and coves the skin-contact surface of the absorbent core. Cuffs (not shown) may be provided on the top sheet.

The back sheet covers the non-skin-contact surface of the absorbent core, and is made of a liquid-impermeable resin sheet. The end portions of the absorbent body C in the vertical direction Y are bonded to the around-torso portions T1, T2. The around-torso portions T1, T2 protrude from the absorbent body C in the girth direction X.

As clearly shown in FIG. 1(c), the around-torso portions T1, T2 are provided with around-torso and around-leg elastic members FT, F2, FL for making the worn article 1 fit to the wearer. The elastic members may be line-shaped or chord-shaped. For example, an elastic member may be a multi-strand member, which is a bunch of rubber threads (elastic fibers). The material of the rubber threads may be polyurethane, for example.

The first around-torso elastic members FT and the second (other) around-torso elastic members F2 may extend in the girth direction X in a straight arrangement and parallel to each other. The elastic members FT, F2, arranged in a straight arrangement and parallel to each other, may be nullified (left with no shrinking force) over an area that overlaps with the absorbent body C.

As clearly shown in FIG. 1(c), a plurality of around-leg elastic members FL are arranged parallel to each other and in a wave-like pattern along lower edge outlines 10E of the around-torso portions T1, T2. The lower edge outline 10E becomes the lower edge when worn.

Note that the around-torso portions T1, T2 are each a stretchable sheet 10.

The absorbent body C of FIG. 1(a) may be formed with a narrowed portion (not shown) where the absorbent body C is narrowed along the crotch of the wearer. The crotch portion 22 may be provided with further around-leg elastic members made of, for example, rubber threads, or the like, for conformity around the legs of the wearer.

The absorbent body C is bonded to the skin-contact surface of the around-torso portions T1, T2.

As used herein, the "skin-contact surface" refers to a surface that faces the skin of the wearer when the worn article 1 is worn, and the "non-skin-contact surface" refers to the surface opposite to the skin-contact surface.

Next, the details of the around-torso portions T1, T2 formed by the stretchable sheet 10 will be described.

The stretchable sheet 10 of the worn article has the skin-contact surface to be in contact with the skin of the wearer and the non-skin-contact surface opposite to the skin-contact surface.

The stretchable sheet 10 includes first and second around-torso webs 11, 12, an around-leg web 13 and elastic members FT, F2, FL layered together. The first around-torso elastic members FT are welded and secured between the first around-torso web 11 and the second around-torso web 12. On the other hand, the second around-torso elastic members F2 and the around-leg elastic members FL are bonded by an adhesive and secured between the first around-torso web 11 and the around-leg web 13.

A plurality of first around-torso elastic members FT are arranged between the pair of webs 11, 12 and are arranged spaced apart from each other as indicated by broken lines in FIG. 1(c).

Due to the shrinking force of the elastic members, the stretchable sheet 10 forms a large number of folds with the elastic members being shrunk, thereby fitting to the skin of the wearer. The first around-torso elastic members FT of FIG. 1(b) are arranged between the non-skin-contact surface, which is a first surface 31, of the first around-torso web 11 and the second around-torso web 12. The area of the second around-torso web 12 to be the upper edge is folded back and bonded to the skin-contact surface, which is a second surface 32, of the first around-torso web 11.

The second around-torso elastic members F2 and the around-leg elastic members FL of FIG. 1(b) are arranged between the pair of webs 11, 13 and are spaced apart from each other as indicated by broken lines in FIG. 1(c). The second around-torso elastic members F2 and the around-leg elastic members FL are arranged between the skin-contact surface, which is the second surface 32, of the first around-torso web 11 and the around-leg web 13 of FIG. 1(b).

With the three webs 11 to 13 layered as described above, a folded-back edge 12E of the second around-torso web 12 and an upper edge 13E of the around-leg web 13 are not visible on the non-skin-contact surface of the worn article, thus improving the appearance.

On the other hand, the absorbent body C of FIG. 1(a) is provided so as to bridge between the front around-torso portion T1 and the rear around-torso portion T2 so as to cover a part of the upper edge 13E of the around-leg web 13. Therefore, the upper edge 13E of the around-leg web 13 does not contact the front torso or the rear torso of the wearer, thus improving the feel (wearability).

Next, an example of a method for manufacturing a worn article will be described with reference to FIG. 2 to FIG. 5.

Figure 3:
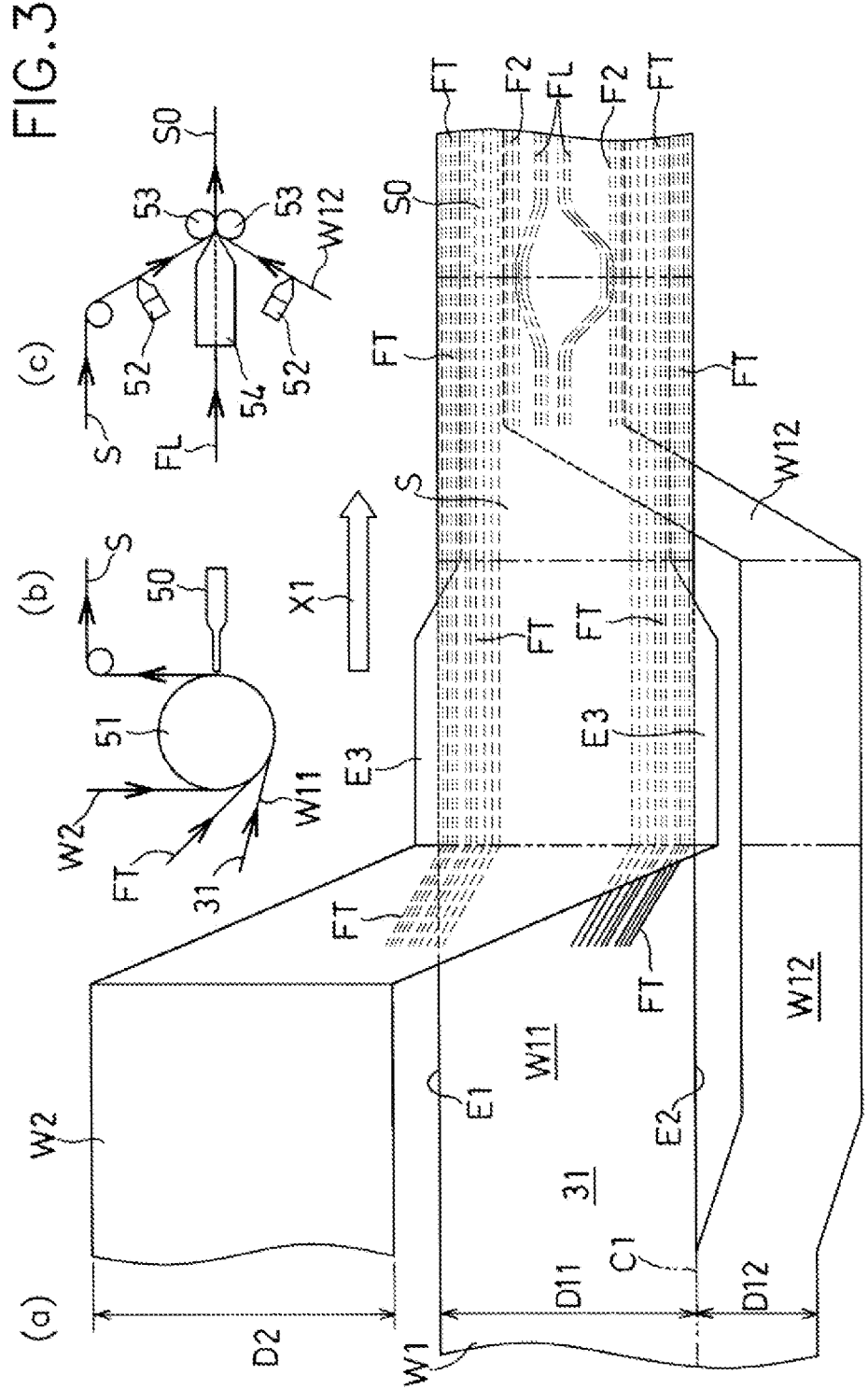
FIG. 3(a) is a schematic plan view showing, partially in perspective, an early period of the method for manufacturing a worn article.
FIG. 3(b) and FIG. 3(c) are schematic side views showing the welding step and the bonding step, respectively.
Figure 4:
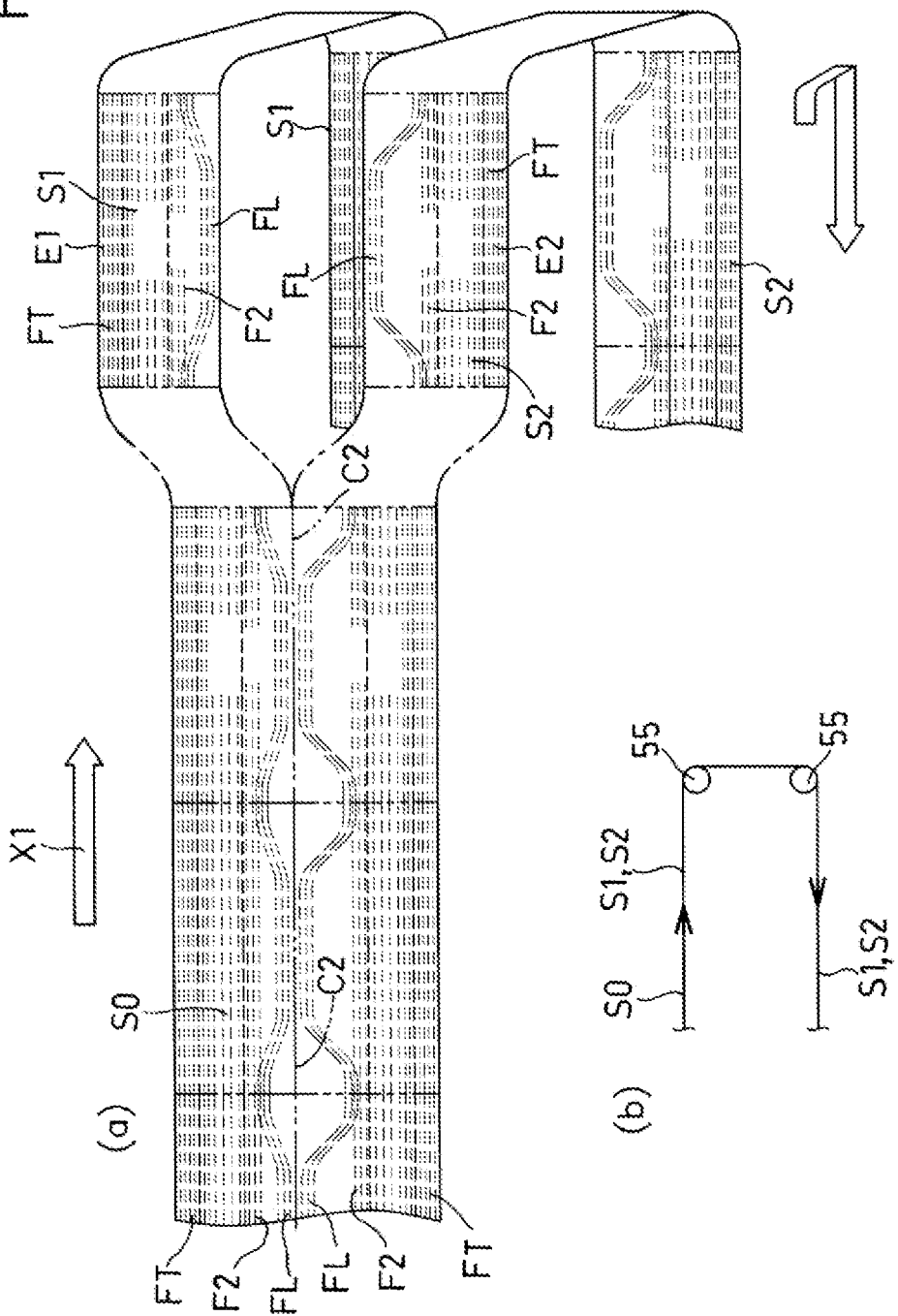
FIG. 4(a) is a schematic plan view showing, partially in perspective, a middle period of the method for manufacturing a worn article.
FIG. 4(b) is a side view showing a turn roller for turning the carrying direction.

Note that in FIG. 3 to FIG. 5, units of individual worn articles are visibly indicated by two-dot-chain lines extending in the width direction, which is orthogonal to the carrying direction of the semi-finished product.

As shown in FIG. 3(a), first, the first and second continuous webs W1, W2 are continuously carried in the predetermined carrying direction (girth direction) X1. While being carried, the first slitting step of slitting the first continuous web W1 along the virtual first cut-off line C1 extending in the carrying direction X1, thereby dividing the first continuous web W1 into a wider first divided web W11 and a narrower second divided web W12 is performed. The width D11 of the first divided web W11 is greater than the width D12 of the second divided web W12. The width D2 of the second continuous web W2 is greater than the width D11 of the first divided web W11.

The first around-torso elastic members FT being stretched extending in the girth direction X (the carrying direction X1) are sandwiched between the wider first divided web W11 and the second continuous web W2, and the welding step of welding together the first divided web W11, the second continuous web W2 and the first around-torso elastic members FT intermittently in the carrying direction X1, thereby producing a layered sheet S, is performed.

As shown in FIG. 3(b), the webs W11, W2 and the first around-torso elastic members FT are introduced between an ultrasonic horn 50 and an anvil roll 51. The horn 50, in cooperation with the anvil roll 51, ulstrasonically welds the pair of webs W11, W2 together, and welds the around-torso elastic members FT to the pair of webs, thus holding the around-torso elastic members FT with the pair of webs. Note that the welding step may be performed by using heat sealing instead of ultrasonic welding.

The width D11 of the wider first divided web W11 of FIG. 3(a) is smaller than the width D2 of the second continuous web W2, and the first divided web W11 has first and second side edges E1, E2 along the carrying direction X1.

After the welding step, the folding back step of folding a pair of third side edges E3 along the carrying direction X1 of the second continuous web W2 so as to wrap the first and second side edges E1, E2 of the first divided web W11 is performed.

On the other hand, the bonding step is performed by sandwiching a plurality of second around-torso elastic members F2, separate from the first around-torso elastic members FT, and around-leg elastic members FL between the layered sheet S and the narrower second divided web W12 while the second around-torso elastic members F2 and the around-leg elastic members FL are stretched, and attaching these members together by an adhesive, thereby producing a stretchable continuous sheet S0.

A plurality of second around-torso elastic members F2 extend straight along the carrying direction X1 and parallel to each other. On the other hand, the around-leg elastic members FL extend along a predetermined wave-like pattern while meandering relative to the carrying direction X1, and are arranged in a periodic wave-like pattern.

As shown in FIG. 3(c), prior to the bonding step described above, an adhesive is applied from an applicator 52 to the layered sheet S and the second divided web W12, and then the around-leg elastic members FL are introduced between a pair of nip rolls 53, 53 while being arranged between the layered sheet S and the second divided web W12. An introducer 54 guides the around-leg elastic members FL while repeatedly reciprocating in the axial direction of the nip rolls 53, 53 so that the around-leg elastic members FL extend while meandering in a predetermined wave-like pattern as shown in FIG. 3(a).

In the welding step described above of FIG. 3, the first around-torso elastic members FT are arranged along the first and second side edges E1, E2 along the carrying direction X1 of the layered sheet S. On the other hand, in the bonding step of producing the stretchable continuous sheet S0, the second around-torso elastic members F2 and the around-leg elastic members FL are arranged in a central area between a first side edge E1 and a second side edge E2 of the layered sheet S.

After the bonding step, the second slitting step of slitting the stretchable continuous sheet S0 of FIG. 4(a) along the virtual second cut-off line C2 along the carrying direction X1 to produce first and second divided sheets S1, S2 is performed. The first divided sheet S1 is to be the front around-torso portion T1 including a part of the around-leg elastic members FL, a part of the around-torso elastic members FT, F2, and the first side edge E1 (FIG. 1(c)). On the other hand, the second divided sheet S2 is to be the rear around-torso portion T2 including the remaining part of the around-leg elastic members FL, the remaining part of the around-torso elastic members FT, F2, and the second side edge E2 (FIG. 1(c)).

The first around-torso elastic members FT and the second around-torso elastic members F2 of the stretchable continuous sheet S0 obtained by the welding and bonding steps described above may be nullified by being cut off, for example, in an area where the absorbent body C is arranged (FIG. 5), as well known in the art.

As shown in FIG. 3(b) and FIG. 2(e), in the welding step described above, the second continuous web W2 is layered on the first surface 31 of the first divided web W11. As shown in FIG. 2(f), in the folding back step described above, the third side edges E3 of the second continuous web W2 are folded so as to overlap with the second surface 32 of the first divided web W11. On the other hand, as shown in FIG. 2(g), in the bonding step described above, the second divided web W12 is bonded to the second surface 32 of the first divided web W11.

After the second slitting step of FIG. 4(a), the width-increasing step of carrying a first and second divided sheets S1, S2 so that a pair of divided sheets S1, S2 move away from each other is performed. Then, the divided sheets S1, S2 are spaced apart from each other.

As shown in FIG. 4(b), the divided sheets S1, S2 may be redirected by redirection rollers 55 so that the divided sheets S1, S2 are carried upside down as shown in FIG. 4(a), for example.

The bridging step to be described below is performed after the width-increasing step. In the bridging step shown in FIG. 5, the absorbent bodies C to be the crotch portions 22 are intermittently provided so as to bridge between the first divided sheet S1 and the second divided sheet S2.

In the bonding step of producing the stretchable continuous sheet S0 of FIG. 3, the around-leg elastic members FL are arranged in a periodic wave-like pattern as will be described below.

The around-leg elastic members FL are arranged so that the around-leg elastic members FL arranged on the first divided sheet S1 and the around-leg elastic members FL arranged on the second divided sheet S2 of FIG. 4(a) extend close to each other in areas where the absorbent bodies C of FIG. 5C bridge, and the around-leg elastic members FL arranged on the first divided sheet S1 and the around-leg elastic members FL arranged on the second divided sheet S2 extend away from each other in areas between the adjacent absorbent bodies C (FIG. 5).

The divided sheets S1, S2 of FIG. 5 are trimmed between adjacent absorbent bodies C so that the edge to be the lower edge when worn (the lower edge outline 10E) is trimmed along the curve of the around-leg elastic members FL, thereby producing a continuous laminate S3. Note that trimming is not always necessary.

For example, the layered sheet S of FIG. 3(a) may be divided in two along a wave-like cut-off line with the around-leg elastic members FL arranged so as to extend along the wave-like shape. Trimming may be performed at any point in time after the production of the stretchable continuous sheet S0.

In FIG. 5, after the bridging step described above, the continuous laminate S3 is folded in two at the absorbent body C so that the first divided sheet S1 and the second divided sheet S2 overlap with each other, and the first side edge E1 and the second side edge E2 overlap with each other. After this folding step, the continuous laminate S3 is severed along the virtual third cut-off line C3 indicated by a two-dot-chain line, and the first divided sheet S1 and the second divided sheet S2 are welded together in the vicinity of the third cut-off line C3, thus achieving so-called seal.

Individual worn articles are produced as described above. Note that while the present example is an example of a pants-type worn article, it may be a diaper-type worn article including fasteners or tapes provided on the worn article of FIG. 1(a).

While a preferred embodiment has been described above with reference to the drawings, various obvious changes and modifications will readily occur to those skilled in the art upon reading the present specification.

For example, the present worn article does not need to include cuffs, or the like. The tension of the elastic members may be nullified even in areas of the around-torso portion other than areas thereof that overlap with the absorbent body.

The around-torso portion does not need to be produced while being slit in two.

Thus, such changes and modifications shall fall within the scope of the present invention as defined by the appended claims.

INDUSTRIAL APPLICABILITY

The present invention is applicable to worn articles of various types such as a pants type and a diaper type.

REFERENCE SIGNS LIST

W1: First continuous web, W2: Second continuous web
W11: First divided web, W12: Second divided web
C: Absorbent body, C1: First cut-off line, C2: Second cut-off line, C3: Third cut-off line
D11, D12, D2: Width
E1: First side edge, E2: Second side edge, E3: Third side edge
FL: Around-leg elastic member, FT: (First) around-torso elastic member, F2: Another (second) around-torso elastic member
S: Layered sheet, S0: Stretchable continuous sheet, S1: First divided sheet, S2: Second divided sheet, S3: Continuous laminate
T1: Front around-torso portion, T2: Rear around-torso portion, X: Girth direction, X1: Carrying direction
1: Worn article, 10: Stretchable sheet, 10E: Lower edge outline
11: First around-torso web, 12: Second around-torso web, 12E: Edge
13: Around-leg web, 13E: Upper edge
22: Crotch portion, 31: First surface, 32: Second surface
50: Horn, 51: Anvil roll
52: Applicator, 53: Nip roll, 54: Introducer, 55: Redirection roller

The invention claimed is:

1. A method for manufacturing a worn article, comprising:
a step of carrying a first continuous web and a second continuous web in a predetermined carrying direction;
a first slitting step of slitting the first continuous web along a virtual first cut-off line extending in the carrying direction, thereby dividing the first continuous web into a wider first divided web and a narrower second divided web;
a step of sandwiching an around-torso elastic member extending in a girth direction between the wider first divided web and the second continuous web;
a welding step of welding together the first divided web, the second continuous web and the around-torso elastic member intermittently in the carrying direction, thereby producing a layered sheet; and
a bonding step of sandwiching an around-leg elastic member meandering relative to the carrying direction between the layered sheet and the narrower second divided web, and attaching the around-leg elastic member thereto by an adhesive, thereby producing a stretchable continuous sheet, wherein:
in the welding step, the around-torso elastic member is arranged along a first side edge and a second side edge along the carrying direction of the layered sheet;
in the bonding step of producing the stretchable continuous sheet, the around-leg elastic member is arranged in a central area between the first side edge and the second side edge of the layered sheet.

2. The manufacturing method according to claim 1, wherein:
a width of the wider first divided web is smaller than a width of the second continuous web, and the first divided web has a first side edge and a second side edge along the carrying direction; and
the method further comprises a folding back step of folding a pair of third side edges along the carrying direction of the second continuous web so as to wrap the first and second side edges of the first divided web.

3. The manufacturing method according to claim 2, wherein:
in the welding step, the second continuous web is layered on a first surface of the first divided web;
in the folding back step, the third side edges of the second continuous web are folded so as to overlap with a second surface of the first divided web; and
in the bonding step, the second divided web is bonded to the second surface of the first divided web.

4. The manufacturing method according to claim 3, wherein:
in the bonding step of producing the stretchable continuous sheet, another around-torso elastic member extending straight along the carrying direction is further sandwiched between the layered sheet and the narrower second divided web, and attached thereto by the adhesive, thereby producing the stretchable continuous sheet.

5. The manufacturing method according to claim 4, wherein:
the first and second continuous webs are made of a thermoplastic resin; and
the welding step is performed by ultrasonic welding or heat sealing.

6. The manufacturing method according to claim 3, wherein:
the first and second continuous webs are made of a thermoplastic resin; and
the welding step is performed by ultrasonic welding or heat sealing.

7. The manufacturing method according to claim 2, wherein:
in the bonding step of producing the stretchable continuous sheet, another around-torso elastic member extending straight along the carrying direction is further sandwiched between the layered sheet and the narrower second divided web, and attached thereto by the adhesive, thereby producing the stretchable continuous sheet.

8. The manufacturing method according to claim 7, wherein:
the first and second continuous webs are made of a thermoplastic resin; and the welding step is performed by ultrasonic welding or heat sealing.

9. The manufacturing method according to claim 2, wherein:
the first and second continuous webs are made of a thermoplastic resin; and
the welding step is performed by ultrasonic welding or heat sealing.

10. The manufacturing method according to claim 1, wherein:
the method further comprises a second slitting step of slitting the stretchable continuous sheet along a virtual second cut-off line along the carrying direction, thereby producing a first divided sheet and a second divided sheet,
the first divided sheet being to be a front around-torso portion including a part of the around-leg elastic member, the around-torso elastic member arranged on the first side edge, and the first side edge, and
the second divided sheet being to be a rear around-torso portion including a remaining part of the around-leg elastic member, the around-torso elastic member arranged on the second side edge, and the second side edge.

11. The manufacturing method according to claim 10, further comprising a bridging step of intermittently providing absorbent bodies so as to bridge between the first divided sheet and the second divided sheet,
each of the absorbent bodies connecting together the front around-torso portion and the rear around-torso portion and being to be a crotch portion.

12. The manufacturing method according to claim 11, wherein the around-leg elastic member is arranged in a periodic wave-like pattern in the bonding step of producing the stretchable continuous sheet so that the around-leg elastic member arranged on the first divided sheet and the around-leg elastic member arranged on the second divided sheet extend close to each other in an area where each of the absorbent bodies bridges, and the around-leg elastic member arranged on the first divided sheet and the around-leg elastic member arranged on the second divided sheet extend away from each other in an area between adjacent absorbent bodies of the absorbent bodies.

13. The manufacturing method according to claim 12, wherein:
in the bonding step of producing the stretchable continuous sheet, another around-torso elastic member extending straight along the carrying direction is further sandwiched between the layered sheet and the narrower second divided web, and attached thereto by the adhesive, thereby producing the stretchable continuous sheet.

14. The manufacturing method according to claim 13, wherein:
the first and second continuous webs are made of a thermoplastic resin; and
the welding step is performed by ultrasonic welding or heat sealing.

15. The manufacturing method according to claim 12, wherein:
the first and second continuous webs are made of a thermoplastic resin; and
the welding step is performed by ultrasonic welding or heat sealing.

16. The manufacturing method according to claim 11, wherein:
in the bonding step of producing the stretchable continuous sheet, another around-torso elastic member extending straight along the carrying direction is further sandwiched between the layered sheet and the narrower second divided web, and attached thereto by the adhesive, thereby producing the stretchable continuous sheet.

17. The manufacturing method according to claim 16, wherein:
the first and second continuous webs are made of a thermoplastic resin; and
the welding step is performed by ultrasonic welding or heat sealing.

18. The manufacturing method according to claim 11, wherein:
the first and second continuous webs are made of a thermoplastic resin; and
the welding step is performed by ultrasonic welding or heat sealing.

19. The manufacturing method according to claim 10, wherein:
in the bonding step of producing the stretchable continuous sheet, another around-torso elastic member extending straight along the carrying direction is further sandwiched between the layered sheet and the narrower second divided web, and attached thereto by the adhesive, thereby producing the stretchable continuous sheet.

20. The manufacturing method according to claim 19, wherein:
the first and second continuous webs are made of a thermoplastic resin; and
the welding step is performed by ultrasonic welding or heat sealing.

21. The manufacturing method according to claim 10, wherein:
the first and second continuous webs are made of a thermoplastic resin; and
the welding step is performed by ultrasonic welding or heat sealing.

22. The manufacturing method according to claim 1, wherein:
in the bonding step of producing the stretchable continuous sheet, another around-torso elastic member extending straight along the carrying direction is further sandwiched between the layered sheet and the narrower second divided web, and attached thereto by the adhesive, thereby producing the stretchable continuous sheet.

23. The manufacturing method according to claim 22, wherein:
the first and second continuous webs are made of a thermoplastic resin; and
the welding step is performed by ultrasonic welding or heat sealing.

24. The manufacturing method according to claim 1, wherein:
the first and second continuous webs are made of a thermoplastic resin; and
the welding step is performed by ultrasonic welding or heat sealing.

* * * * *